(12) United States Patent
Smith et al.

(10) Patent No.: US 8,940,007 B2
(45) Date of Patent: Jan. 27, 2015

(54) TROCAR ASSEMBLY WITH OBTURATOR DISSECTOR

(75) Inventors: Robert C. Smith, Middletown, CT (US); Gregory Okoniewski, North Haven, CT (US); Russell Heinrich, Madison, CT (US)

(73) Assignee: Covidien LP, Mansfield, MA (US)

( * ) Notice: Subject to any disclaimer, the term of this patent is extended or adjusted under 35 U.S.C. 154(b) by 150 days.

(21) Appl. No.: 12/594,833

(22) PCT Filed: Apr. 16, 2008

(86) PCT No.: PCT/US2008/060418
§ 371 (c)(1),
(2), (4) Date: Oct. 6, 2009

(87) PCT Pub. No.: WO2008/130966
PCT Pub. Date: Oct. 30, 2008

(65) Prior Publication Data
US 2010/0063450 A1 Mar. 11, 2010

Related U.S. Application Data

(60) Provisional application No. 60/925,113, filed on Apr. 18, 2007.

(51) Int. Cl.
*A61B 17/34* (2006.01)

(52) U.S. Cl.
CPC ......... *A61B 17/3496* (2013.01); *A61B 17/3417* (2013.01); *A61B 2017/3454* (2013.01); *A61B 2017/3456* (2013.01); *A61B 2017/346* (2013.01); *A61B 17/3494* (2013.01)
USPC .......................................... 606/185; 606/190

(58) Field of Classification Search
CPC . A61B 17/34; A61B 17/3417; A61B 17/3494

USPC ................ 606/184, 185; 604/164.01, 164.06, 604/164.08, 164.11, 164.12, 165.01, 165.04
See application file for complete search history.

(56) References Cited

U.S. PATENT DOCUMENTS 3,841,329 A * 10/1974 Killinger ....................... 604/231
4,535,773 A 8/1985 Yoon (Continued)

FOREIGN PATENT DOCUMENTS

| EP | 0 617 924 | 2/1994 |
| EP | 0 604 197 | 6/1994 |

(Continued)

OTHER PUBLICATIONS

European Search Report, Application No. EP 07252535, dated Feb. 17, 2009.

*Primary Examiner* — Kathleen Holwerda
*Assistant Examiner* — Sarah W Aleman

(57) ABSTRACT

A surgical system for penetrating tissue includes an obturator including an obturator housing and an obturator member extending from the obturator housing. The obturator member defines a longitudinal axis along which the obturator extends from trailing to leading ends thereof, and has a leading penetrating member adapted to penetrate tissue. The penetrating member defines, from leading to trailing, a cylindrical element having a generally arcuate leading surface and a generally planar dissecting element extending from the cylindrical portion. The obturator member and the leading penetrating member may be monolithically formed. The obturator member may include an obturator rod connected to the obturator housing, and defining a generally "t"-shaped cross-section. The generally planar dissecting element defines side surfaces obliquely arranged with respect to the longitudinal axis. The side surfaces may be arcuate or may define cutting edges.

24 Claims, 18 Drawing Sheets

(56) References Cited

U.S. PATENT DOCUMENTS

| | | | | |
|---|---|---|---|---|
| 4,601,710 A | | 7/1986 | Moll | |
| 4,654,030 A | | 3/1987 | Moll et al. | |
| 4,902,280 A | | 2/1990 | Lander | |
| 4,931,042 A | | 6/1990 | Holmes et al. | |
| 5,030,206 A | | 7/1991 | Lander | |
| 5,066,288 A | | 11/1991 | Deniega et al. | |
| 5,104,382 A | | 4/1992 | Brinkerhoff et al. | |
| 5,114,407 A | | 5/1992 | Burbank | |
| 5,116,353 A | | 5/1992 | Green | |
| 5,152,754 A | | 10/1992 | Plyley et al. | |
| 5,158,552 A | | 10/1992 | Borgia et al. | |
| 5,215,526 A | | 6/1993 | Deniega et al. | |
| 5,224,952 A | | 7/1993 | Deniega et al. | |
| 5,226,426 A | | 7/1993 | Yoon | |
| 5,226,891 A | | 7/1993 | Bushatz et al. | |
| 5,232,440 A | | 8/1993 | Wilk | |
| 5,246,425 A | | 9/1993 | Hunsberger et al. | |
| 5,248,298 A | | 9/1993 | Bedi et al. | |
| 5,263,937 A | | 11/1993 | Shipp | |
| 5,275,583 A | | 1/1994 | Crainich | |
| 5,290,243 A | | 3/1994 | Chodorow et al. | |
| 5,295,993 A | | 3/1994 | Green | |
| 5,312,354 A | | 5/1994 | Allen et al. | |
| 5,314,417 A | | 5/1994 | Stephens et al. | |
| 5,318,580 A | | 6/1994 | Gresl, Jr. | |
| 5,318,585 A | | 6/1994 | Guy et al. | |
| 5,338,305 A | | 8/1994 | Pluylet et al. | |
| 5,346,459 A | | 9/1994 | Allen | |
| 5,350,393 A | | 9/1994 | Yoon | |
| 5,356,421 A | | 10/1994 | Castro | |
| 5,364,365 A | | 11/1994 | Wortrich | |
| 5,364,372 A | | 11/1994 | Danks et al. | |
| 5,366,445 A | | 11/1994 | Haber et al. | |
| 5,370,625 A | | 12/1994 | Shichman | |
| 5,372,588 A | * | 12/1994 | Farley et al. | 606/181 |
| 5,387,197 A | | 2/1995 | Smith et al. | |
| 5,399,167 A | | 3/1995 | Deniega | |
| 5,411,515 A | | 5/1995 | Haber et al. | |
| 5,431,635 A | | 7/1995 | Yoon | |
| 5,437,643 A | | 8/1995 | Transue | |
| 5,441,513 A | | 8/1995 | Roth | |
| 5,462,532 A | | 10/1995 | Gresl | |
| 5,471,705 A | | 12/1995 | Dao | |
| 5,474,539 A | | 12/1995 | Costa et al. | |
| 5,478,317 A | | 12/1995 | Yoon | |
| 5,486,190 A | | 1/1996 | Green | |
| 5,487,745 A | | 1/1996 | McKenzie | |
| 5,522,833 A | | 6/1996 | Stephens et al. | |
| 5,527,335 A | | 6/1996 | Bolduc et al. | |
| 5,533,977 A | | 7/1996 | Metcalf et al. | |
| 5,538,509 A | | 7/1996 | Dunlap et al. | |
| 5,545,150 A | | 8/1996 | Danks et al. | |
| 5,549,564 A | | 8/1996 | Yoon | |
| 5,554,137 A | | 9/1996 | Young et al. | |
| 5,554,167 A | | 9/1996 | Young et al. | |
| 5,569,160 A | | 10/1996 | Sauer et al. | |
| 5,578,053 A | | 11/1996 | Yoon | |
| 5,591,190 A | | 1/1997 | Yoon | |
| 5,607,440 A | | 3/1997 | Danks et al. | |
| 5,609,604 A | * | 3/1997 | Schwemberger et al. | 606/185 |
| 5,624,459 A | | 4/1997 | Kortenbach et al. | |
| 5,626,598 A | | 5/1997 | Roth | |
| 5,645,556 A | | 7/1997 | Yoon | |
| 5,645,557 A | | 7/1997 | Yoon | |
| 5,658,236 A | | 8/1997 | Sauer et al. | |
| 5,669,885 A | | 9/1997 | Smith | |
| 5,674,237 A | | 10/1997 | Ott | |
| 5,676,156 A | | 10/1997 | Yoon | |
| 5,690,663 A | | 11/1997 | Stephens | |
| 5,690,664 A | | 11/1997 | Sauer et al. | |
| 5,697,913 A | | 12/1997 | Sierocuk et al. | |
| 5,709,671 A | | 1/1998 | Stephens et al. | |
| 5,772,660 A | | 6/1998 | Young et al. | |
| 5,776,112 A | | 7/1998 | Stephens et al. | |
| 5,797,943 A | | 8/1998 | Danks et al. | |
| 5,817,061 A | * | 10/1998 | Goodwin et al. | 604/164.03 |
| 5,827,315 A | | 10/1998 | Yoon | |
| 5,843,115 A | * | 12/1998 | Morejon | 606/185 |
| 5,851,216 A | | 12/1998 | Allen | |
| 5,860,996 A | | 1/1999 | Urban et al. | |
| 5,868,773 A | | 2/1999 | Danks et al. | |
| 5,879,332 A | | 3/1999 | Schwemberger et al. | |
| 5,885,256 A | | 3/1999 | Chern et al. | |
| 5,893,369 A | | 4/1999 | LeMole | |
| 5,904,699 A | | 5/1999 | Schwemberger et al. | |
| 5,913,848 A | | 6/1999 | Luther et al. | |
| 5,916,232 A | | 6/1999 | Hart | |
| 5,947,930 A | | 9/1999 | Schwemberger et al. | |
| 5,980,493 A | | 11/1999 | Smith et al. | |
| 5,984,941 A | | 11/1999 | Wilson et al. | |
| 5,997,510 A | | 12/1999 | Schwemberger | |
| 6,017,356 A | | 1/2000 | Frederick et al. | |
| 6,022,367 A | | 2/2000 | Sherts | |
| 6,030,402 A | | 2/2000 | Thompson et al. | |
| 6,036,657 A | | 3/2000 | Milliman et al. | |
| 6,036,711 A | | 3/2000 | Mozdzierz et al. | |
| 6,063,099 A | | 5/2000 | Danks et al. | |
| 6,099,544 A | | 8/2000 | Wolf et al. | |
| 6,228,058 B1 | | 5/2001 | Dennis et al. | |
| 6,238,407 B1 | | 5/2001 | Wolf | |
| 6,319,226 B1 | | 11/2001 | Sherry | |
| 6,319,266 B1 | * | 11/2001 | Stellon et al. | 606/185 |
| 6,497,687 B1 | | 12/2002 | Blanco | |
| 6,497,716 B1 | | 12/2002 | Green et al. | |
| 6,544,277 B1 | | 4/2003 | O'Heeron et al. | |
| 6,613,063 B1 | | 9/2003 | Hunsberger | |
| 6,656,198 B2 | | 12/2003 | Tsonton et al. | |
| 6,685,630 B2 | | 2/2004 | Sauer et al. | |
| 6,716,201 B2 | | 4/2004 | Blanco | |
| 6,719,746 B2 | | 4/2004 | Blanco | |
| 6,830,578 B2 | | 12/2004 | O'Heeron et al. | |
| 6,835,201 B2 | | 12/2004 | O'Heeron et al. | |
| 6,837,874 B1 | | 1/2005 | Popov | |
| 6,960,164 B2 | | 11/2005 | O'Heeron | |
| D518,177 S | | 3/2006 | Blanco | |
| D531,726 S | | 11/2006 | Blanco et al. | |
| 7,320,694 B2 | * | 1/2008 | O'Heeron | 606/167 |
| 7,419,496 B2 | * | 9/2008 | Staudner | 606/185 |
| 2003/0100914 A1 | | 5/2003 | O'Heeron et al. | |
| 2003/0109894 A1 | | 6/2003 | Blanco | |
| 2004/0230155 A1 | | 11/2004 | Blanco et al. | |
| 2004/0230217 A1 | | 11/2004 | O'Heeron | |
| 2005/0038466 A1 | | 2/2005 | O'Heeron et al. | |
| 2005/0065543 A1 | | 3/2005 | Kahle et al. | |
| 2005/0119676 A1 | | 6/2005 | Bumbalough et al. | |
| 2005/0203559 A1 | | 9/2005 | O'Heeron | |
| 2005/0209623 A1 | | 9/2005 | Patton | |
| 2005/0261717 A1 | | 11/2005 | Sauer et al. | |
| 2006/0030870 A1 | | 2/2006 | Staudner | |
| 2006/0149302 A1 | | 7/2006 | Popov | |
| 2006/0173479 A1 | | 8/2006 | Smith | |
| 2006/0200095 A1 | | 9/2006 | Steube | |
| 2006/0200182 A1 | | 9/2006 | Prosek | |
| 2007/0005087 A1 | | 1/2007 | Smith et al. | |
| 2007/0010842 A1 | | 1/2007 | Popov | |
| 2007/0016237 A1 | | 1/2007 | Smith | |

FOREIGN PATENT DOCUMENTS

| | | |
|---|---|---|
| EP | 0 769 279 | 4/1997 |
| WO | 94/04206 | 3/1994 |
| WO | 94/22508 | 3/1994 |
| WO | 9404082 | 3/1994 |
| WO | 02/11605 | 2/2002 |

* cited by examiner

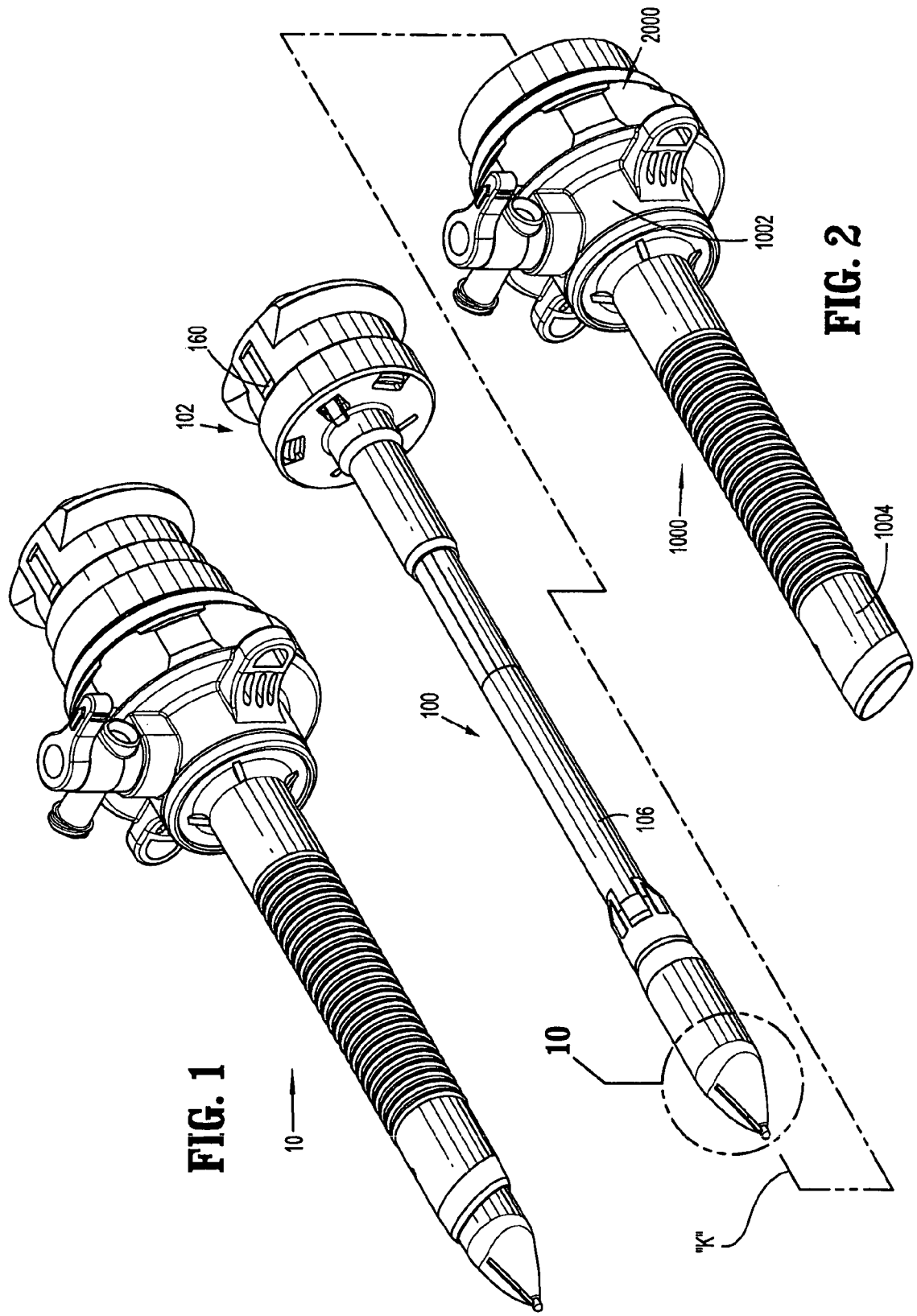

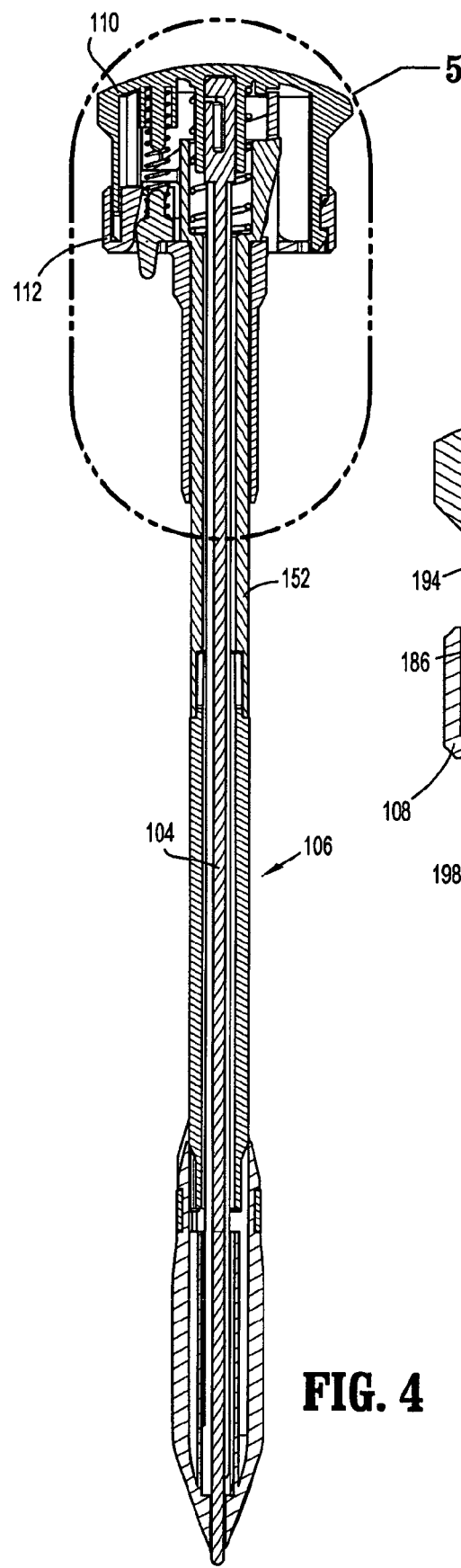
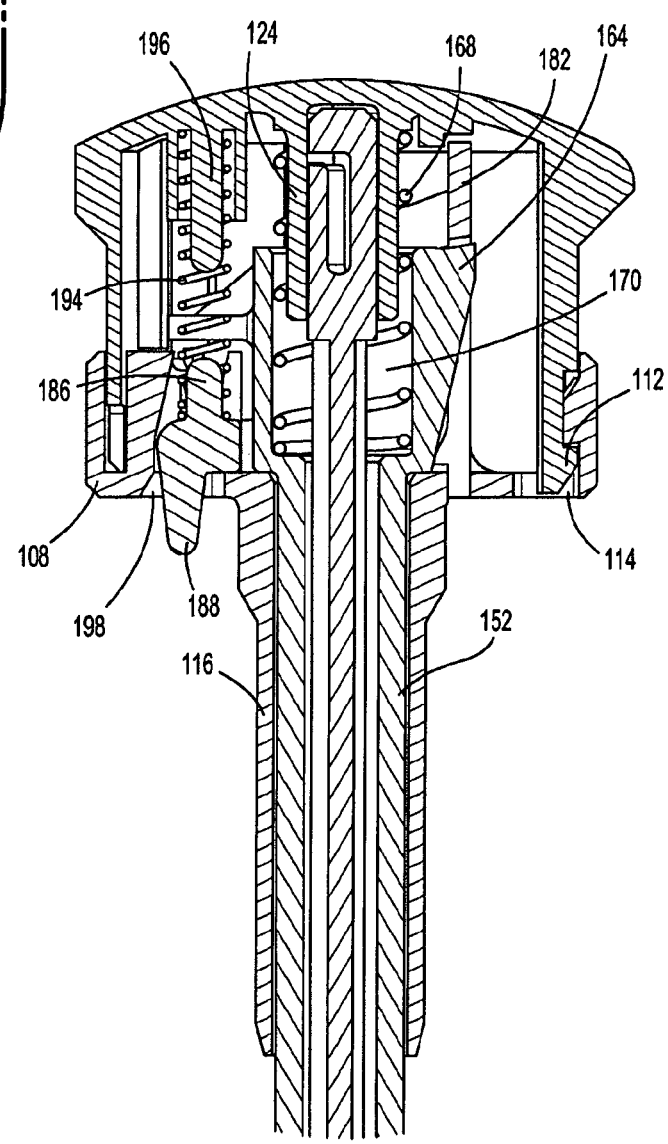
FIG. 4  FIG. 5

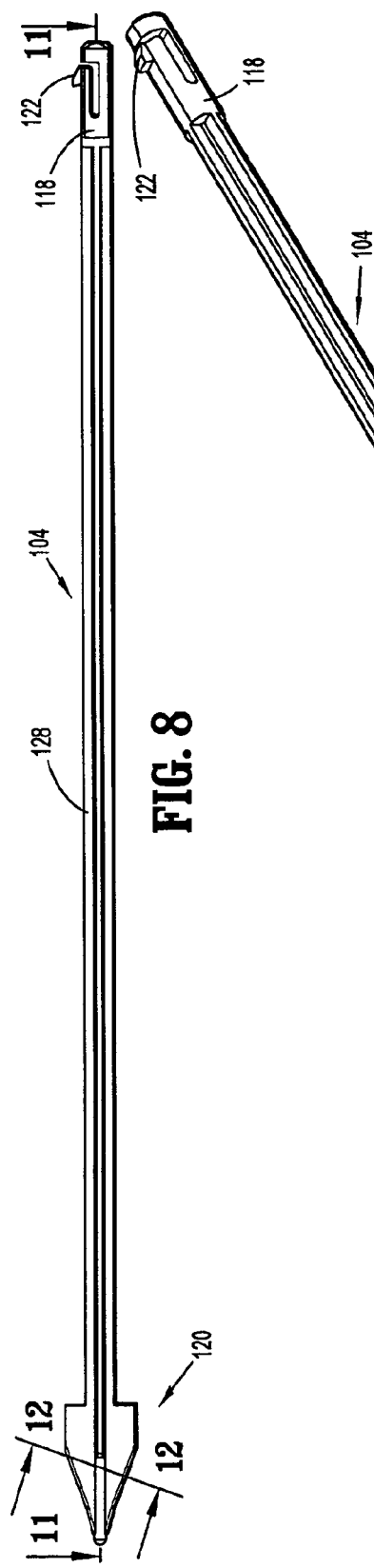
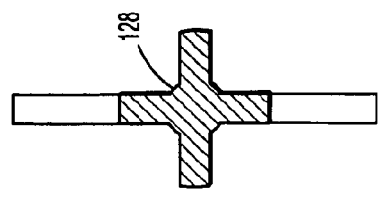
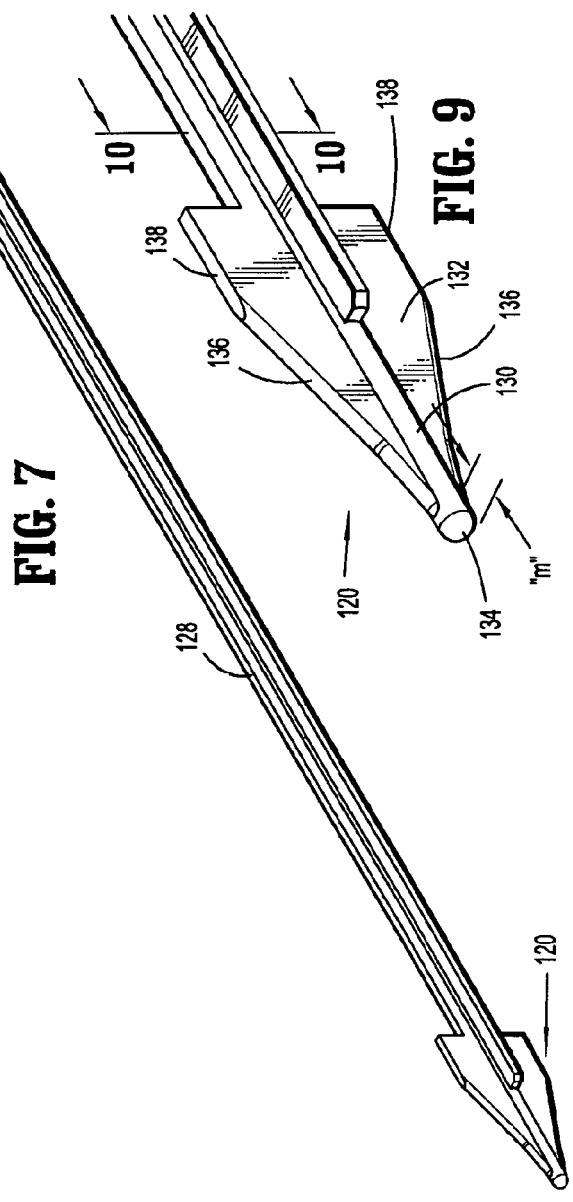
FIG. 8
FIG. 10
FIG. 7
FIG. 9

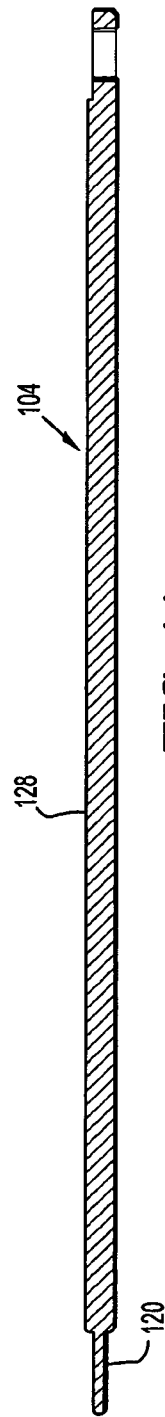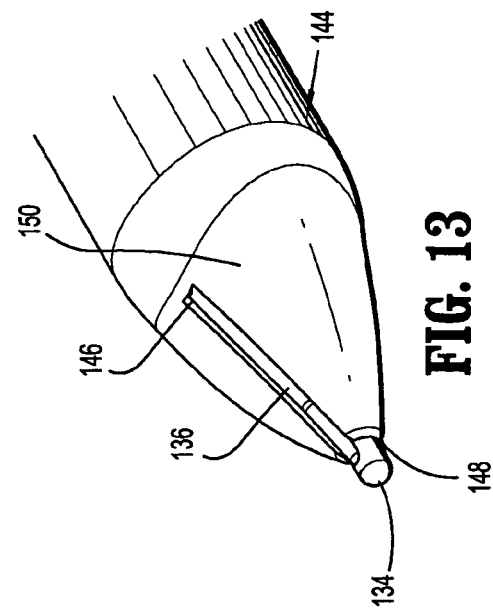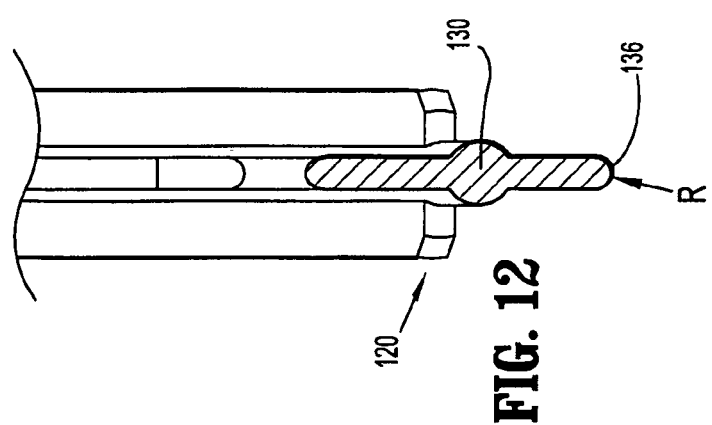

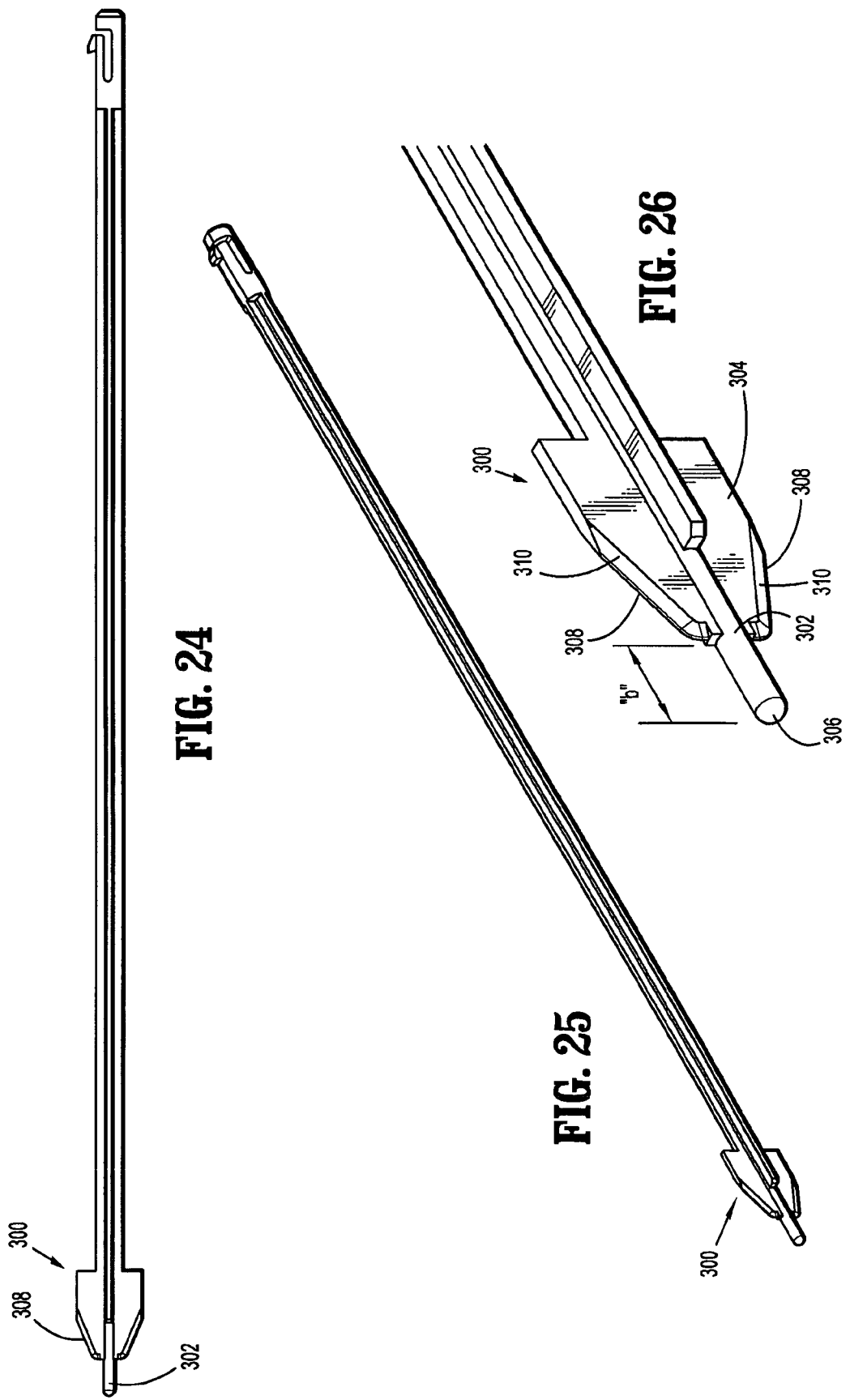

TROCAR ASSEMBLY WITH OBTURATOR DISSECTOR

CROSS REFERENCE TO RELATED APPLICATIONS

This application is a National Stage Application of PCT/US2008/060418 filed Apr. 16, 2008 under 35 USC §371 (a), which claims priority of U.S. Provisional Patent Application Ser. No. 60/925,113 filed Apr. 18, 2007 the entire contents of which are hereby incorporated by reference.

BACKGROUND OF THE RELATED ART

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, the trocar assemblies with seal mechanisms are utilized to provide the necessary pathway to the surgical site while minimizing leakage of insufflation gases.

Trocar assemblies typically include an obturator which is removably inserted through a cannula. The obturator may include a safety shield which protects against unintentional puncturing by the sharpened tip of the obturator. The safety shield includes a mechanism which controls the relative movement and locking of the safety shield. One example of a safety shield mechanism is disclosed in commonly assigned U.S. Pat. No. 6,319,266 to Stellon et al., the entire contents of which are hereby incorporated by reference.

SUMMARY

Accordingly, the present disclosure is directed to a surgical system for penetrating tissue. The system includes an obturator having an obturator housing and an obturator member extending from the obturator housing. The obturator member defines a longitudinal axis along which the obturator extends from trailing to leading ends thereof, and has a leading penetrating member adapted to penetrate tissue. The penetrating member defines, from leading to trailing, a cylindrical element having a generally arcuate leading surface and a generally planar dissecting element extending from the cylindrical portion. The obturator member and the leading penetrating member may be monolithically formed. The obturator member may include an obturator rod connected to the obturator housing, and defining a generally "t"-shaped cross-section. The generally planar dissecting element defines side surfaces obliquely arranged with respect to the longitudinal axis. The side surfaces may be arcuate or may define cutting edges.

An outer member may be mounted about the obturator member. The outer member is adapted for longitudinal movement between a first position corresponding to a first operative condition of the penetrating member and a second position corresponding to a second operative condition of the penetrating member. The outer member may be normally biased toward the first position. The penetrating member may be dimensioned whereby the cylindrical element and the side surfaces each are at least partially exposed from the outer member when the outer member is in the second position. The penetrating member may be dimensioned whereby the cylindrical element is at least partially exposed from the outer member when the outer member is in the first position, to assist in initial dissection of tissue.

The surgical system may include a cannula defining a longitudinal axis and having a longitudinal opening therethrough for at least partial reception of the obturator. A latch member is associated with the obturator housing, and moveable from an initial position securing the outer member in the first position to a release position permitting the outer member to move to the second position. A release member is mounted to the obturator housing and operatively coupled with the latch member. The release member is adapted to move the latch member to the release position during positioning of the obturator within the longitudinal opening of the cannula.

The obturator housing may include a housing base and a housing cover. The housing cover is adapted for rotation about the longitudinal axis between a lock position preventing movement of the outer member to the retracted position and a lock release position permitting the outer member to move to the retracted position.

BRIEF DESCRIPTION OF THE DRAWINGS

Preferred embodiments of the present disclosure are described hereinbelow with references to the drawings, wherein:

FIG. 1 is a perspective view of a trocar assembly in accordance with the principles of the present disclosure;

FIG. 2 is a perspective view with parts separated of the trocar assembly illustrating the cannula assembly and the obturator assembly;

FIG. 4 is a side cross-sectional view of the obturator assembly;

FIG. 5 is an enlarged cross-sectional view of the indicated area of detail of FIG. 4;

FIG. 7 is a perspective view of the obturator member;

FIG. 8 is a side cross-sectional of the obturator member;

FIG. 9 is a perspective view of the penetrating member of the obturator member;

FIG. 10 is a cross-sectional view of the obturator rod of the obturator member;

FIG. 11 is a cross-sectional view of the obturator member taken along the lines 11-11 of FIG. 8;

FIG. 12 is a cross-sectional view of the obturator member taken along the lines 12-12 of FIG. 8;

FIG. 13 is a perspective view of the sleeve head of the outer member and the penetrating member;

FIG. 24 is a side plan view of an alternate embodiment of the obturator member;

FIG. 25 is a perspective view of the obturator member of FIG. 24;

FIG. 26 is a perspective view illustrating the penetrating member of the obturator member;

DETAIL DESCRIPTION OF PREFERRED EMBODIMENTS

Figure 3:
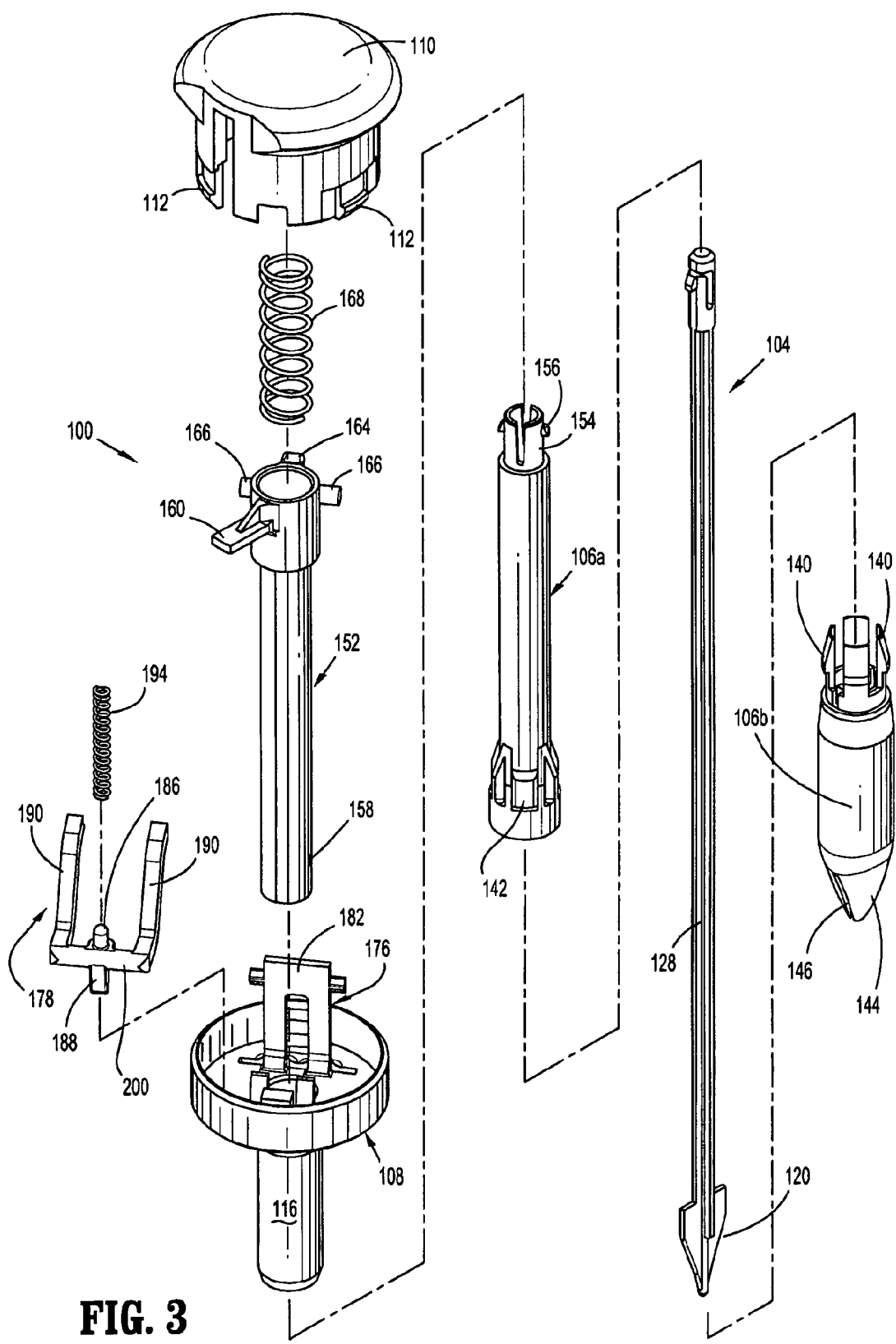
FIG. 3 is a perspective view with parts separated of the obturator assembly illustrating the obturator housing, the obturator member and the outer member.
Figure 6:
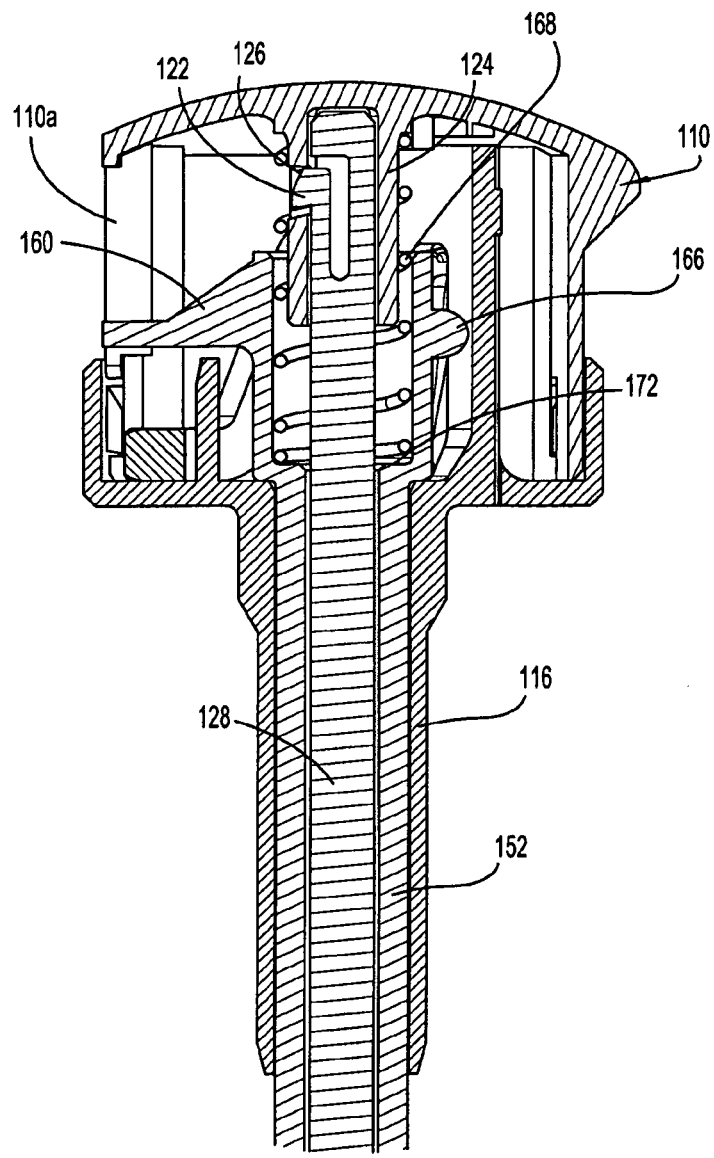
FIG. 6 is a second enlarged cross-sectional view of the obturator housing of the obturator assembly.

Referring now in detail to the drawing figures, in which, like references numerals identify similar or identical elements, there is illustrated, in FIGS. 1 and 2, a trocar assembly constructed in accordance with a preferred embodiment of the present disclosure and designated generally by reference numeral 10. Trocar assembly 10 is particularly adapted for use in minimally invasive surgical procedures such as endoscopic or laparoscopic procedures. Generally, trocar assembly 10 includes two principal subassemblies, namely, obturator assembly 100 and cannula assembly 1000.

Cannula assembly 1000 may be any cannula assembly suitable for use in a laparoscopic surgical procedure. In one preferred embodiment, cannula assembly 1000 includes cannula housing 1002 and cannula sleeve 1004 extending from the cannula housing 1002. Either or both cannula housing 1002 and cannula sleeve 1004 may be transparent in part or in whole and may be fabricated from biocompatible metal or polymeric material. Cannula assembly 1000 may include an internal seal such as a duck-bill valve or other zero closure valve adapted to close in the absence of a surgical instrument to prevent passage of insufflation gases through the cannula assembly 1000.

Trocar assembly 10 may also include a seal assembly 2000 which is preferably releasably mounted to cannula housing 1002. Means for releasably connected seal assembly 2000 to cannula housing 1002 may include a bayonet coupling, threaded connection, latch, friction fit, tongue and groove arrangements, snap-fit, etc. Seal assembly 2000 includes seal housing 2002 and at least one internal seal which is adapted to form a fluid tight seal about an instrument inserted through the seal assembly 2000. One suitable seal may be the fabric seal disclosed in commonly assigned U.S. Pat. No. 6,702,787, which issued Mar. 9, 2004, the entire contents of which are incorporated herein by reference. The seal disclosed in the '630 patent may be a flat septum seal having a first layer of resilient material and a second fabric layer juxtaposed relative to the first layer. Further details of the seal may be ascertained by reference to the '787 patent. Seal assembly 2000 may or may not be a component of cannula assembly 1000. For example, the seal assembly may be a separate, removable assembly. In the alternative, the seal assembly may comprise an integral part of the cannula assembly 1000 and not be removable.

With reference now to FIGS. 3-5, in conjunction with FIG. 2, obturator assembly 100 includes obturator housing 102, elongated obturator member 104 extending distally from the housing 102 and outer member 106 coaxially mounted about the obturator member 104. In general, outer member 106 is adapted to reciprocate or move in a longitudinal direction between an unarmed and armed condition of obturator member 104. Obturator member 104 defines obturator axis "k" and will be discussed in greater detail hereinbelow. Obturator housing 102 includes housing base 108 and housing cover 110. Once the appropriate components are positioned therewithin (as described below), housing base 108 may be attached to housing cover 110 by engaging mating surfaces, for example, by resilient latches 112 of cover 110 interlocking with correspondingly dimensioned latch recesses 114 of housing base 108. Preferably, to uniformly connect base 108 and cover 110 at least three corresponding latches 112 and openings 114 are spaced evenly around the circumference of the cover 110 and the base 108, respectively. Housing base 108 further defines base extension 116.

With reference to FIGS. 6-12, obturator member 104 includes proximal mount 118 at its proximal end and penetrating member 120 at its distal end. Penetrating member 120 will be discussed in greater detail hereinbelow. Proximal mount 118 includes mounting tab 122. Mounting tab 122 is adapted to move radially inwardly upon initial insertion of proximal mount 118 within internal cover extension 124 of housing cover 110, and thereafter return to its initial outward position once the tab 122 is aligned within opening 126 of internal cover extension 124. In this position depicted in FIG. 6, mounting tab 122 is secured within opening 126. Thus, the aforedescribed mounting arrangement of obturator member 104 and obturator cover 110 secures the obturator member 104 from moving in an axial direction relative to obturator housing 102.

Obturator member 104 defines obturator rod 128 extending from proximal mount 118. Obturator rod 128 has a "t" shaped cross-section. The "t" shaped cross-section increases the overall strength of obturator rod 128 and its resistance to bending or flexing. Penetrating member 120 is disposed at the distal end of obturator rod 128. As best depicted in FIG. 9, penetrating member 120 includes, from distal to proximal, cylindrical element 130 and planar dissecting element 132 extending contiguously from the cylindrical element 130. Cylindrical element 130 defines an arcuate or rounded leading surface 134 which is atraumatic to tissue and extends a predetermined distance "m" beyond planar dissecting element 132. This consequent narrow profile provided by cylindrical element 132 permits initial insertion within tissue and facilitates, e.g., dissection or advancement, within the tissue without an incising action. Cylindrical element 132 may extend through planar dissecting element 132 to obturator rod 128. Planar dissecting element 132 defines a triangular arrangement having oblique side surfaces 136 leading to parallel end surfaces 138. Side surfaces 136 may be arcuate or rounded as shown to be atraumatic to tissue. In the alternative, side surfaces 136 may be sharpened. End surfaces 138 may be blunt or sharp.

Obturator member 104 including obturator rod 128 and penetrating member 120 may be integrally, i.e., monolithically formed, as a single unit. In one method, obturator member 104 may be formed of a suitable polymeric material through known injection molding techniques. Grinding processes, with, or without injection molding, are also envisioned. In the alternative, obturator member 104 may be formed of a metal such as stainless steel or titanium.

Referring again to FIGS. 2-4, outer member 106 includes proximal sleeve component 106a and distal sleeve component 106b which is secured to proximal sleeve component 106a. In one embodiment, distal sleeve component 106b includes a plurality of, e.g., four, locking tabs 140 which are received within corresponding openings 142 of proximal sleeve component 106a in snap relation to secure the components. In the alternative, outer member 106 may be integrally formed as a single member. With reference to FIGS. 3 and 13, second sleeve component 106b includes nose 144 which is positioned about penetrating member 120 of obturator member 104. Nose 144 defines a central slot 146 for reception of penetrating member 120. Nose 144 further defines a central aperture 148 communicating with central slot 146 to permit passage of cylindrical element 130 of penetrating member 120. Nose 144 moves relative to penetrating member 120 during longitudinal movement of outer member 106. As best depicted in FIG. 13, in the initial or unarmed condition, nose 144 is positioned relative to penetrating member 120 whereby cylindrical portion 130 of the penetrating member 120 at least partially extends beyond the nose 144. In addition, side surfaces 136 of planar dissecting element 132 also may extend beyond nose 144, i.e., protrude outwardly from central slot 146. Nose 144 may be generally conical in configuration. Alternatively, nose 144 may also have a slight inward contour 150 along opposed peripheral portions. Various other configurations are also envisioned.

Figure 14:
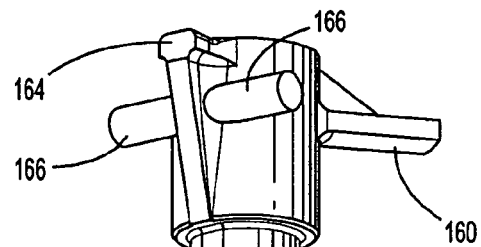
FIG. 14 is a perspective view of the indicator collar of the obturator housing.

Referring now to FIGS. 3-6, in conjunction with FIG. 14, the remaining operative components of obturator assembly will be discussed. Obturator assembly 100 further includes indicator collar 152 positioned within obturator housing 102 and secured to outer member 106. In one preferred arrangement, indicator collar 152 receives proximal end 154 of first sleeve component 106a of outer member 106. Outer member 106 may be fixed within indicator collar 152 through conventional means including cements, adhesives, interference fit, etc. In one embodiment, first sleeve component 106a incorporates locking tabs 156 extending radially outwardly. Locking tabs 156 are received within corresponding opening 158 in indicator collar 152 in snap relation. With this arrangement, indicator collar 152 and outer member 106 move concurrently along the longitudinal axis "k" and relative to obturator housing 102 and obturator member 104 during use of obturator assembly 100.

Indicator collar 152 further includes a position indicator, such as indicator flag 160, extending transversely relative to the indicator collar 152. Indicator flag 160 is visible from the exterior of obturator housing 102 as it extends through groove 110a of housing cover 110 (see also FIGS. 2 and 6). Preferably, indicator flag 160 is colored to contrast sharply with the surrounding housing components. For example, indicator flag 160 may be red if the surrounding housing components are white or light colored. Indicator collar 152 further includes collar ledge 164 and a pair of posts 166 formed below the ledge 164 and extending radially outwardly from the ledge 164. Collar ledge 164 serves to releasably lock outer member 106 in a distal position corresponding to an unarmed condition of obturator assembly 100. FIG. 4 illustrates the unarmed condition of obturator assembly 100.

Referring to FIGS. 3-6, indicator collar 160 and outer member 106 are spring biased in the distal direction by coil spring 168. In particular, coil spring 168 is received within internal bore 170 of indicator collar 152 and engages internal shelf 172 (see FIG. 6) of the indicator collar 152. The proximal end of coil spring 168 is coaxially mounted about cover extension 124 depending from the interior surface of housing cover 110.

Figure 17:
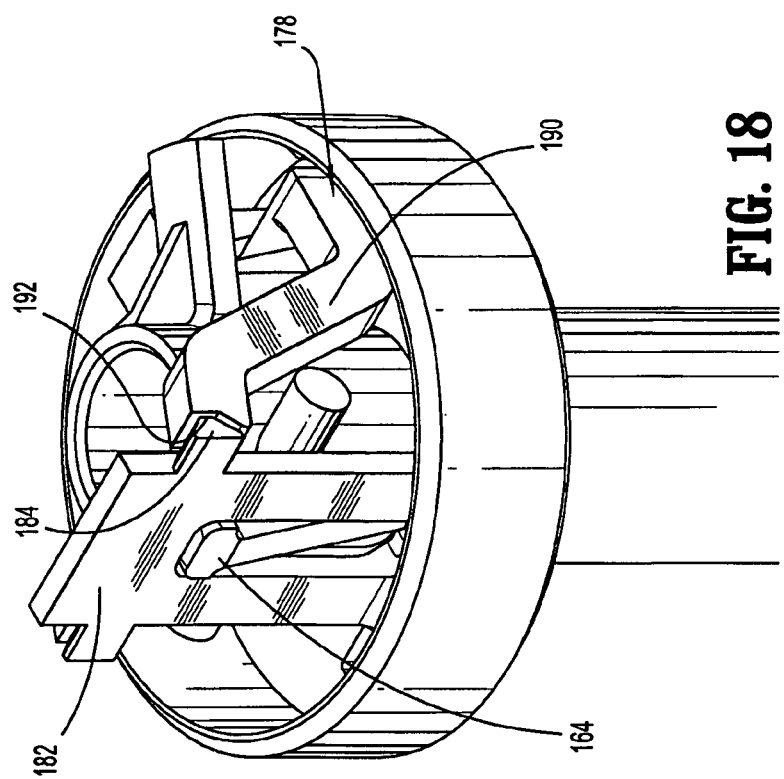
FIGS. 17-18 are perspective views illustrating the components of the latch mechanism.
Figure 18:
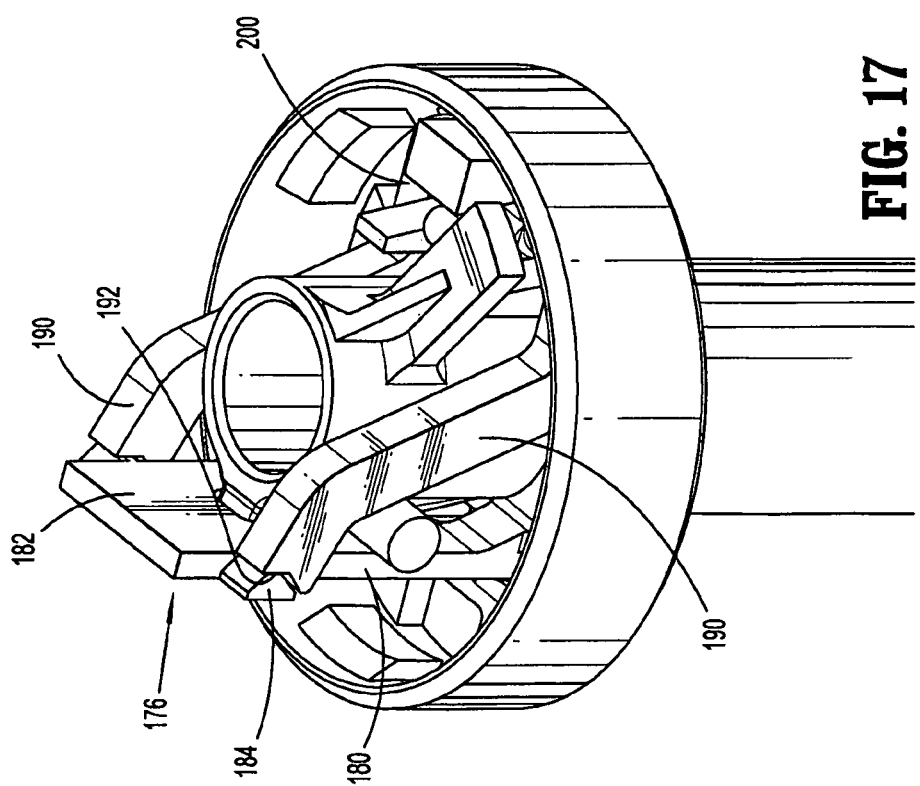

Referring now to FIGS. 14-18, in conjunction with FIGS. 3-5, obturator assembly 100 includes a latching mechanism disposed within obturator housing 102 to prevent proximal movement of outer member 106 until such time as the obturator assembly 100 is mounted to cannula assembly 1000 and the surgeon is prepared to begin trocar entry. Latching mechanism includes latch member 176, and release member such as slider 178, as best seen in FIG. 3. Latch member 176 has two vertical legs 180 connected by web 182. A pair of biasing posts 184 extends outwardly, one for each side of latch member 176. Collar ledge 164 of indicator collar 152 is engaged and secured by web 182 of latch member 176 when in an initial position of the latch member 176 as depicted in FIGS. 17-18. In the initial position of latch member 170, outer member 106 is retained in a first extended position shown in FIG. 4 corresponding to the unarmed or first operative condition of obturator assembly 100. Latch member 176 is preferably molded as part of housing base 106 in cantilever fashion. However, latch member 176 may be formed as a separate element and secured to base 106 by suitable known techniques.

Figure 15:
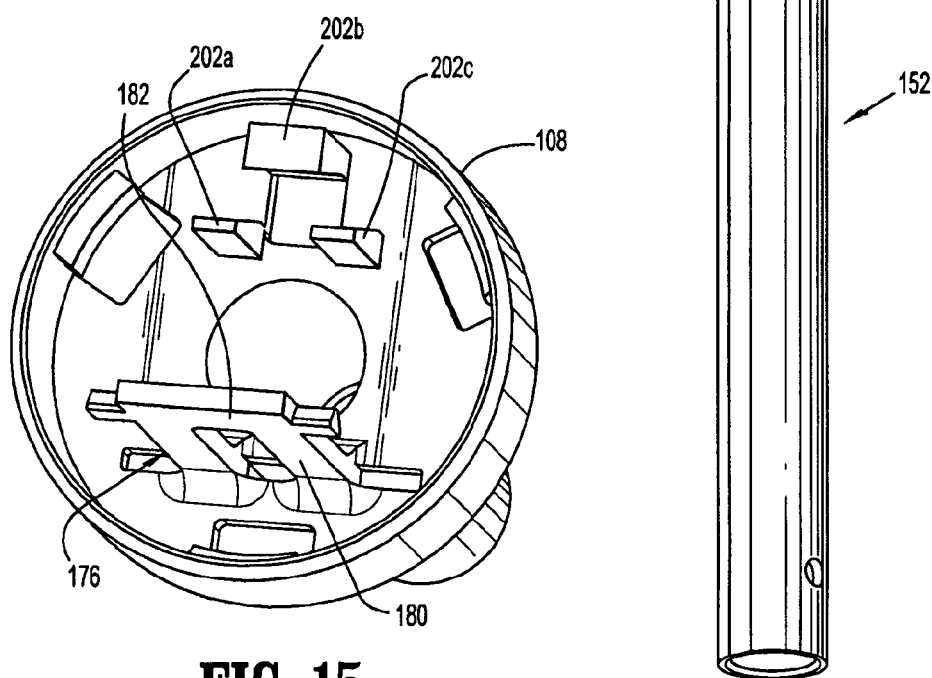
FIG. 15 is a perspective view of the housing base of the obturator housing.
Figure 16:
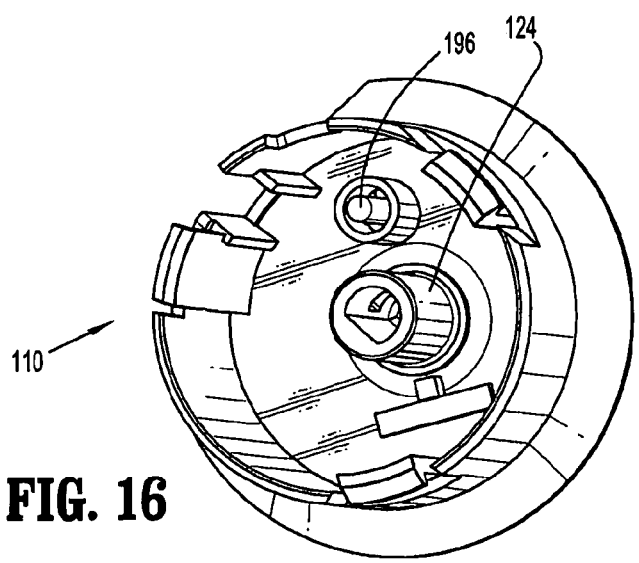
FIG. 16 is a perspective view of the housing cover of the obturator housing.

Slider 178 includes post 186 disposed at its lower end, arming button 188 extending distally from the distal face of slider 178 and a pair of slider legs 190 which terminate in crooks 192. Crooks 192 defined in slider legs 190 are configured and dimensioned to engage posts 184 of latch member 176, as shown in FIGS. 17 and 18. Slider 178 is distally biased by slider spring 194 which is maintained in axial alignment by slider post 186 of slider 178. The proximal end of slider spring 194 bears against the inner surface of housing cover 110 and is maintained in position between proximal post 186 and cylindrical post 196 formed in the housing cover 110 (see FIGS. 5 and 16). The distal biasing of slider 178 causes arming button 188 to project through opening 198 formed in housing base 106. The lower end or transverse leg 200 of slider 178 resides with mounting posts 202 a-c of housing base 106 (FIG. 15). Mounting of obturator assembly 100 relative to cannula assembly 1000 causes slider 178 to translate or rotate generally vertically in a generally proximal direction as will be described further hereinbelow.

Figures 19, 20:
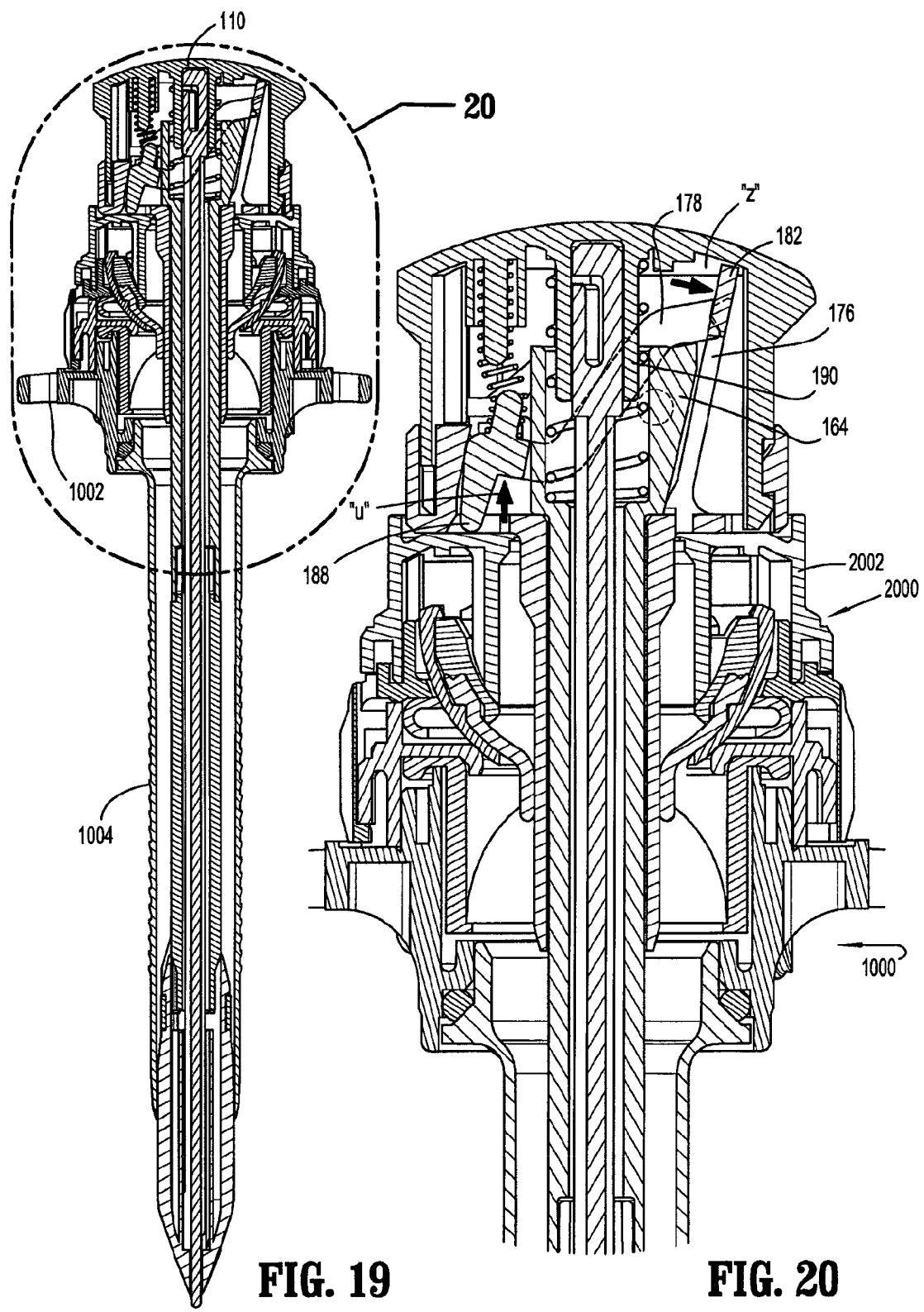
FIG. 19 is a side cross-sectional view of the trocar assembly illustrating the obturator assembly mounted relative to the cannula assembly and the latch member in an actuated position.
FIG. 20 is a view of the indicated area of detail of FIG. 19 illustrating the relationship of the components of the latch member in the actuated position.

With reference now to FIGS. 19-20, a method of use and operation of trocar assembly 10 will be discussed. Obturator assembly 100 is inserted within cannula assembly 1000 and advanced to where obturator housing 102 is approximated with seal housing 2002 of the seal assembly 2000. Seal assembly 2000 may comprise a separate part or may be a component of cannula assembly 1000. Seal housing 2002 and housing base 108 of obturator housing 102 may be appropriately dimensioned to form a friction fit or may be coupled to each other by conventional means including bayonet coupling, tongue-groove, etc. Approximation of obturator housing 102 and seal housing 202 releases outer member 106 from a locked condition, thereby actuating the trocar assembly. In particular, with the obturator housing 102 and seal housing 2002 approximated, arming button 188 of slider 178 engages surface 2004 of seal housing 2002 and is forced upwardly (depicted by directional arrow "u") from the position depicted in FIG. 5 to the position depicted in FIGS. 19-20. During this movement, slider 178 pivots or angulates whereby legs 190 of slider 178 push latch member 176 in a radial outward direction (depicted by directional arrow "z") such that web portion 182 of latch member 176 is out of axial alignment with ledge 164 of indicator collar 152. In this position, indicator collar 152 and outer member 106 are free to axially move.

Figures 21, 22:
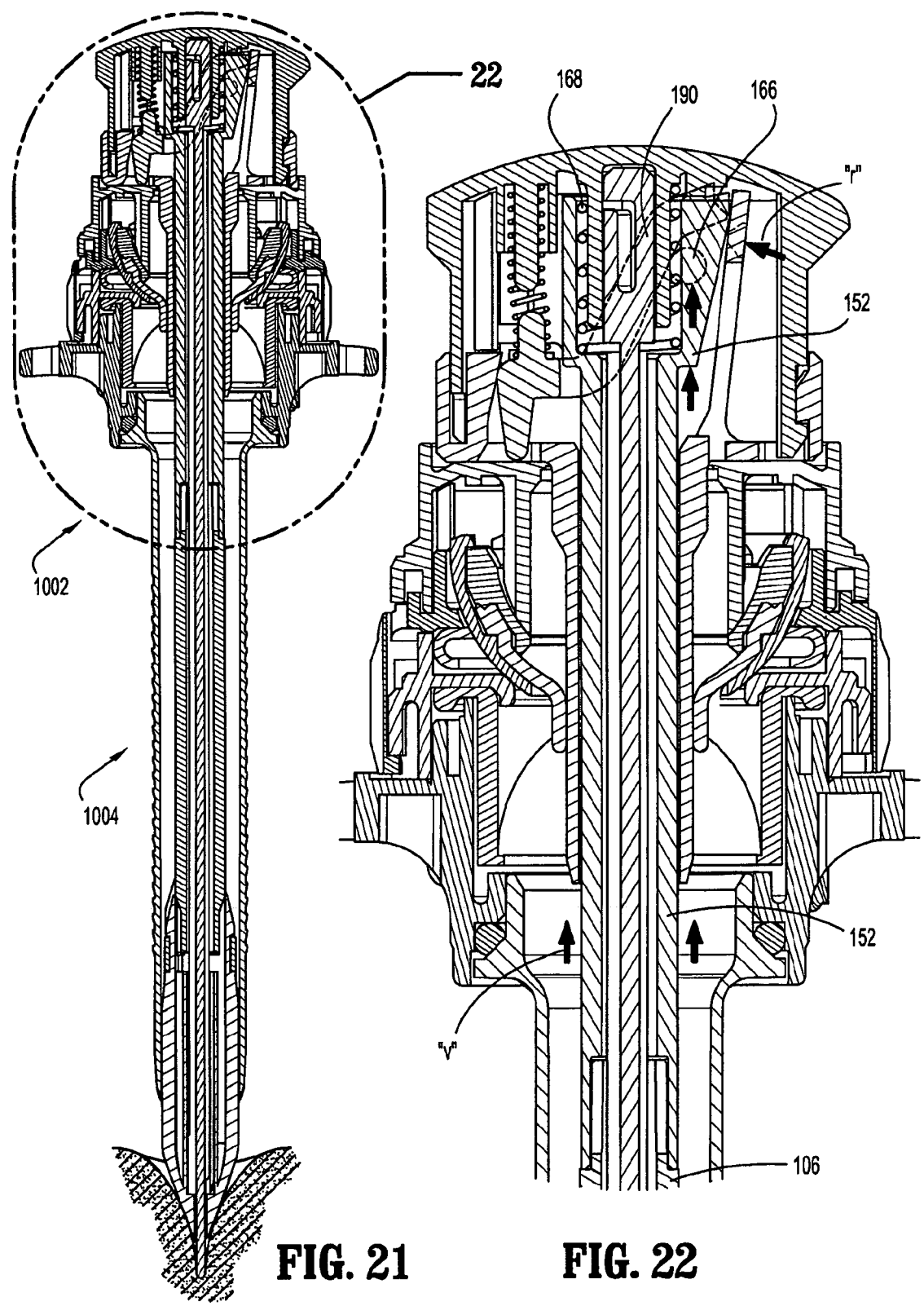
FIG. 21 is a view similar to the view of FIG. 19 illustrating the outer member of the obturator assembly in a retracted position.
FIG. 22 is a view of the indicated area of detail of FIG. 21 illustrating the relationship of the components of the latch member when the outer member is in the retracted position.
Figure 23:
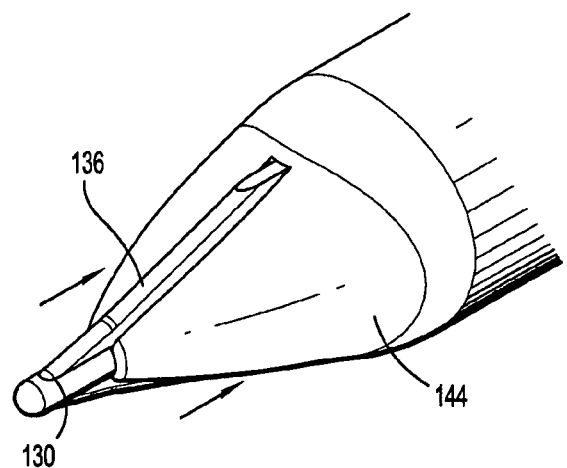
FIG. 23 is a perspective view illustrating retraction of the outer member during insertion within tissue.

Referring now to FIGS. 21-22, the surgeon begins to insert trocar assembly 10 through the body wall of the patient. Nose 144 of outer member 106 contacts the tissue and is driven upwardly to cause outer member 106 and indicator collar 152 to move proximally (depicted by directional arrow "v") against the bias of coil spring 168 corresponding to a second operative condition of the obturator assembly 100. Such movement further exposes cylindrical element 130 of penetrating member 120 of obturator member 104 and exposes, or further exposes side surfaces 136 of the penetrating member 120. FIG. 23 illustrates the armed condition of penetrating member 120. In this position, penetrating member 120 is used in a penetrating, dissecting or piercing capacity to pass through the tissue. This armed condition of obturator assembly 100 is visually verified by the proximal location of indicator flag 160 of indicator collar 152. In addition, proximal movement of indicator collar 152 causes posts 166 of the indicator collar 152 to ride along outer surfaces of legs 190 of slider 178 to thereby move the slider 178 at least radially inwardly and upwardly (as shown by the directional arrows "r") in a general aligned position relative to the obturator axis "k". FIG. 22 illustrates this actuated position of latch member 176. With penetrating member 120 exposed, the surgeon may apply a distally-directed force to obturator assembly 100 to cause penetration through the tissue. It is noted that indicator flag 160 in its proximal position provides visual confirmation of the armed condition of penetrating member 120.

Once penetrating member 120 and nose 150 pass through the body wall of the patient, outer member 106 is no longer subject to a retracting force applied by tissue and, thus, moves distally to assume the unarmed condition depicted in FIG. 4. In particular, indicator collar 152 and outer member 106 are driven distally under the influence of coil spring 148. Concurrently with this movement, slider 178, which is aligned relative to axis "x", is driven distally under the influence of coil spring 194. Upon removal of obturator assembly 100, in the respective positions of indicator collar 152 and slider 178 depicted in FIGS. 4 and 5, collar ledge 164 of indicator collar 152 securely engages web 182 of latch member 176 to secure outer member 106 in the extended position. The obturator assembly 100 is completely removed from cannula assembly 1000 and surgery is performed with instruments inserted through cannula assembly 1000.

With reference to FIGS. 24-26, an alternative embodiment of penetrating member 300 of obturator member 104 is illustrated. In accordance with the embodiment, cylindrical element 302 of penetrating member 300 extends from planar dissecting element 304 for a predetermined distance "b" greater than the corresponding distance of cylindrical element of the embodiment of FIGS. 1-23. With this arrangement, cylindrical element 302 may be manipulated through the relatively narrowed tissue sites to further assist in initial retraction or dissection of the tissue, and positioning of penetrating member 300 relative to the targeted tissue. Cylindrical element 302 terminates in rounded leading surface 306 to be generally atraumatic; however, leading surface 306 may include edges or be pointed to incise tissue. In addition, side surfaces 308 define a triangular configuration having an edge disposed between intersecting surfaces 310. The edge defined at side surfaces 308 may be sharp to facilitate incising or cutting through tissue. In the alternative, side surfaces 308 may be blunt or atraumatic.

Figure 27:
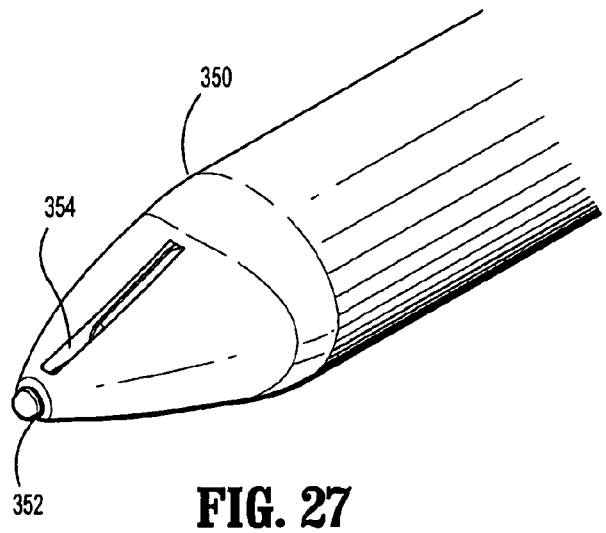
FIG. 27 is a perspective view of the outer member and the penetrating member in an unarmed condition.
Figure 28:
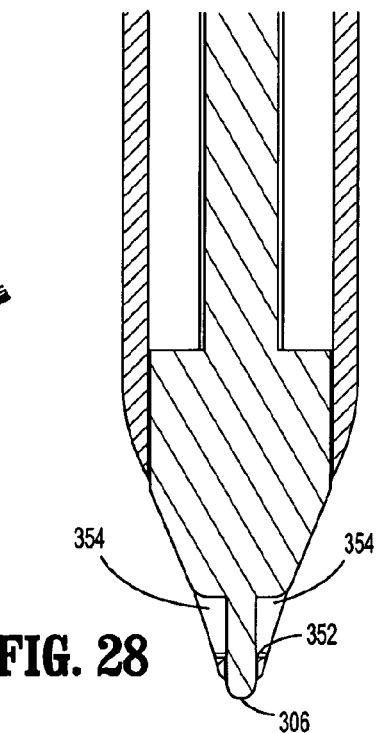
FIG. 28 is a side cross-sectional view of the outer member and the penetrating member in the unarmed condition.
Figure 29:
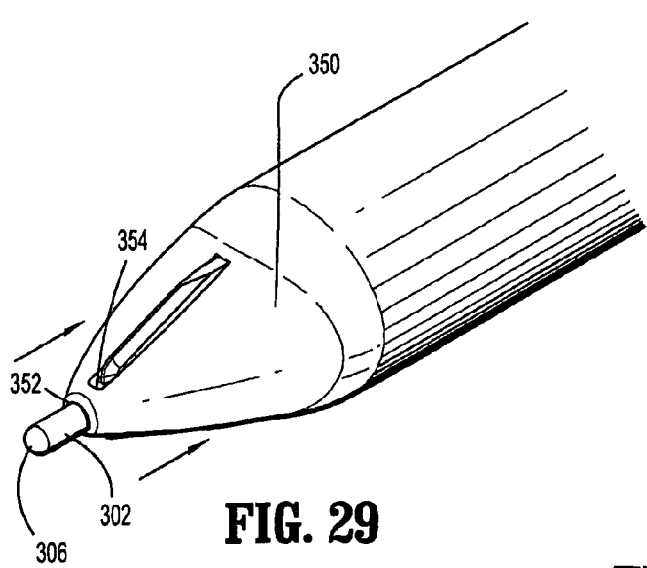
FIG. 29 is a perspective view of the outer member and the penetrating member in the unarmed condition.
Figure 30:
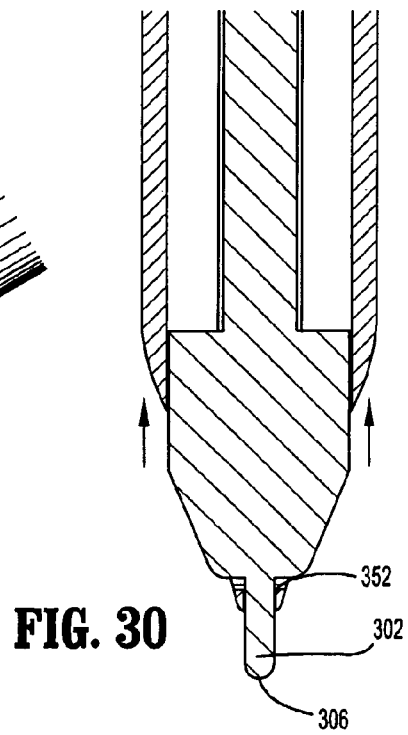
FIG. 30 is a side cross-sectional view of the outer member and the penetrating member in the unarmed condition.
Figure 31:
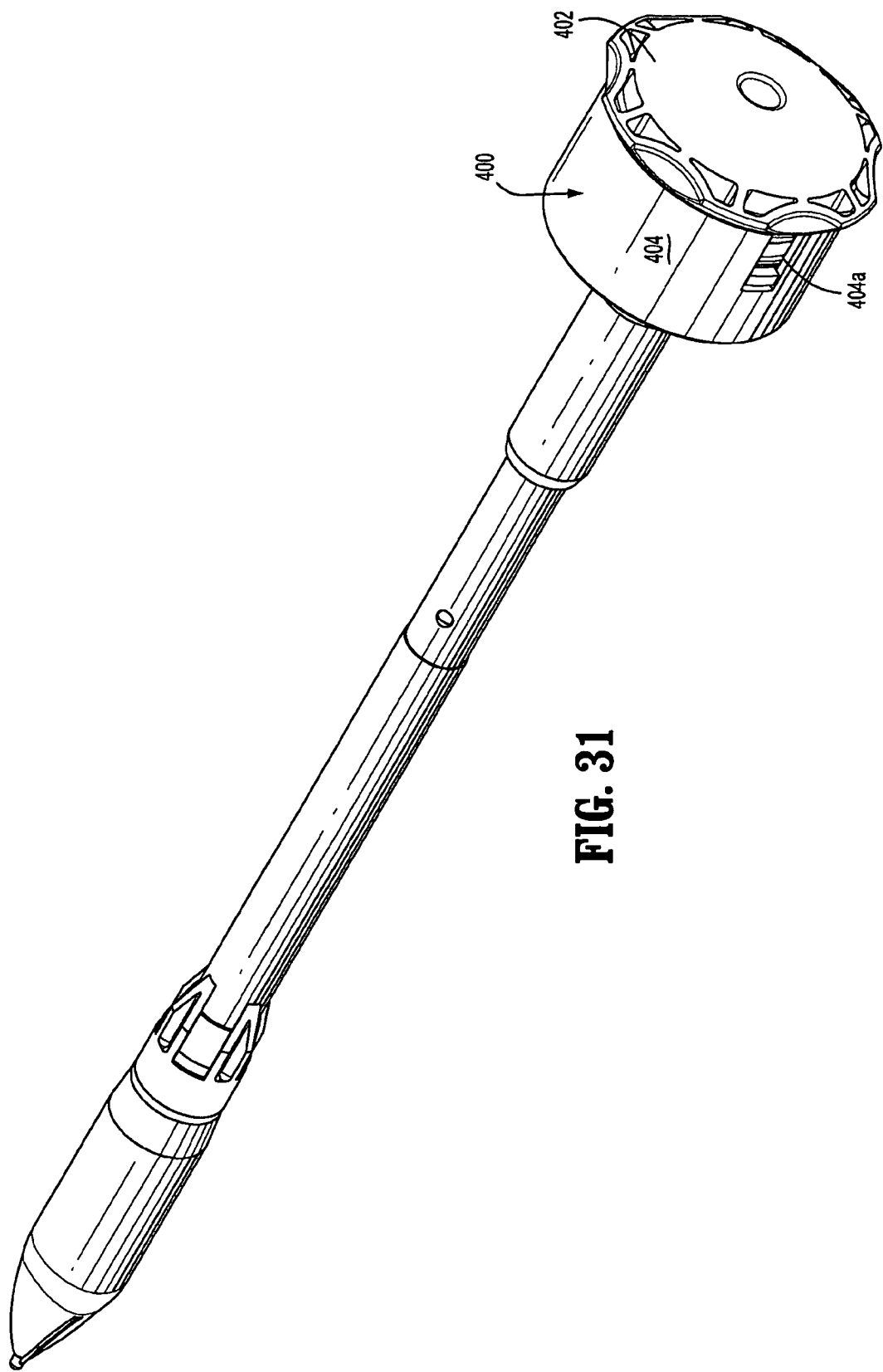
FIG. 31 is a perspective view of an alternate embodiment of obturator assembly including a safety cap to prevent exposure of the dissecting portion of the penetrating member.

FIGS. 27-28 illustrate an alternate embodiment of nose 350 of outer member 106 to be used with penetrating member 300 of FIGS. 24-26. Nose 350 includes central aperture 352 with first and second slots 354 on each side of the central aperture 352 in diametrical opposed relation. Central aperture 352 receives cylindrical element 302 of penetrating member 300 and permits the cylindrical element 302 to slide therewithin. Specifically, portions of nose 350 defining central aperture 352 circumscribe cylindrical element 302 of penetrating member 350. In the first position of nose 350 depicted in FIGS. 27-28, cylindrical element 302 extends partially beyond nose 350. Side surfaces 308 may be confined within first and second slots 354. In a second position of nose 350 when outer member 106 is retracted as depicted in FIGS. 29-30, cylindrical element 302 of penetrating member 300 is further exposed from central aperture 352. Side surfaces 308 also at least partially extend through first and second slots 354. In this position, side surfaces (if sharp) may incise tissue or (if atraumatic) dissect the tissue.

In other respects, obturator member 104 functions in a similar manner to the obturator member 104 of FIGS. 1-23.

Figures 32, 33:
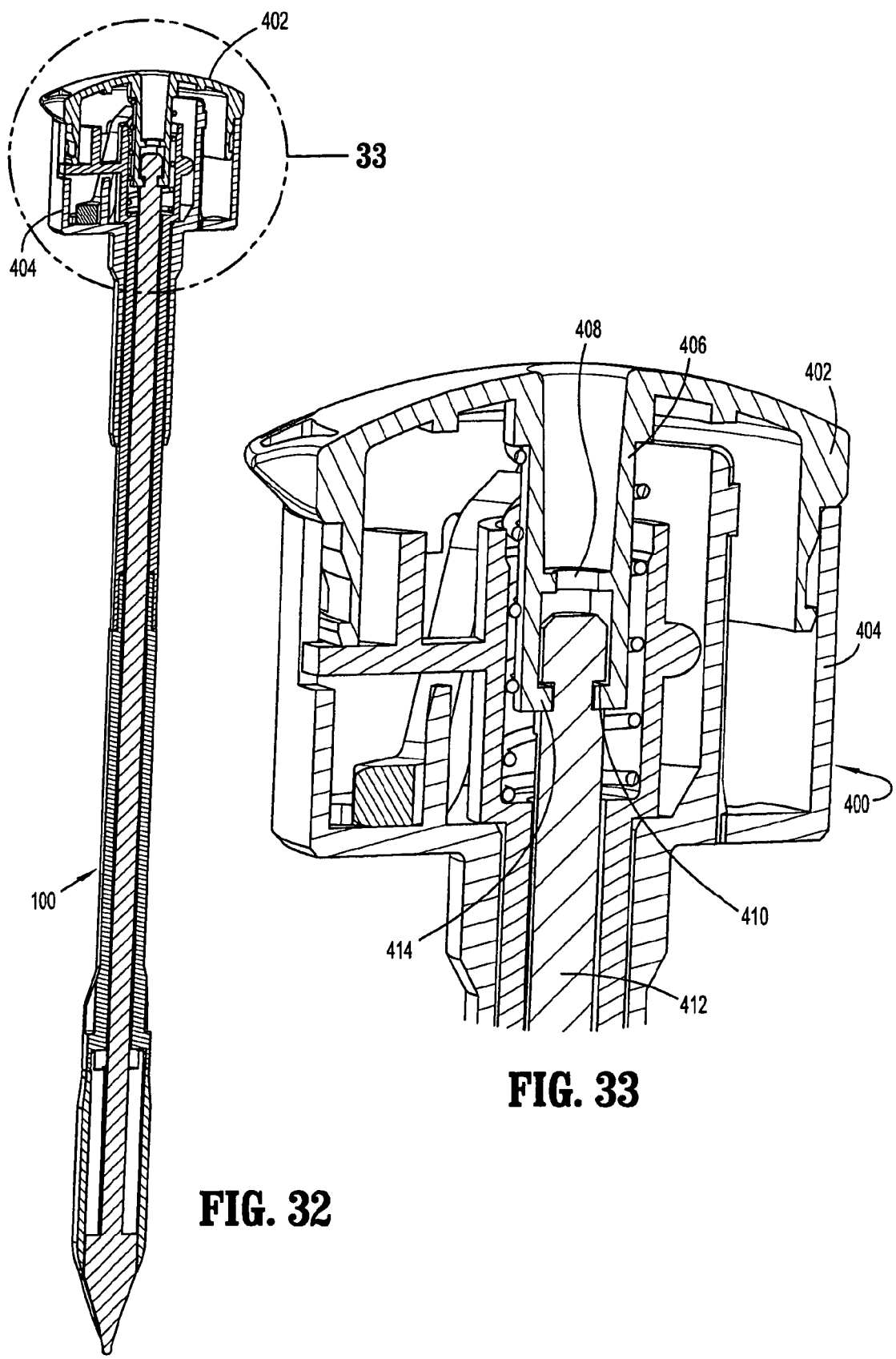
FIG. 32 is a side cross-sectional view of the obturator assembly of FIG. 31.
FIG. 33 is an enlarged view of the area of detail of FIG. 32.

FIGS. 31-38 illustrate another embodiment of the present disclosure. In accordance with this embodiment, obturator housing 400 includes housing cover 402 which is adapted for rotation about longitudinal axis "k". Housing cover 402 is rotatably movable relative to housing base 404 between a first locked position preventing retraction of outer member 106 and a second release position permitting retraction of the outer member 106 to expose penetrating member 120. As best depicted in FIG. 33, housing cover 402 includes internal cylindrical mount 406 which defines a cylindrical cavity 408 for reception of corresponding annular groove 410 of obturator rod 412 whereby the annular groove 410 of the obturator rod 412 is received and supported by an annular wall 414 at the base of the mount 406 to thereby axially fix the components. By virtue of this arrangement, housing cover 402 may rotate relative to obturator rod 412.

Figure 34:
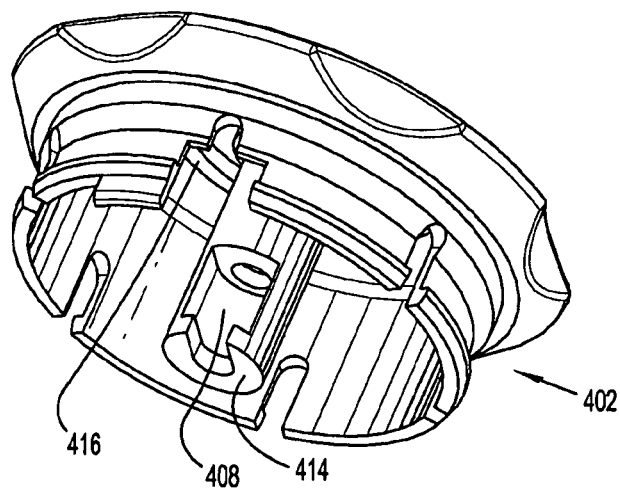
FIG. 34 is a perspective view of the obturator housing cover of the obturator assembly.
Figure 35:
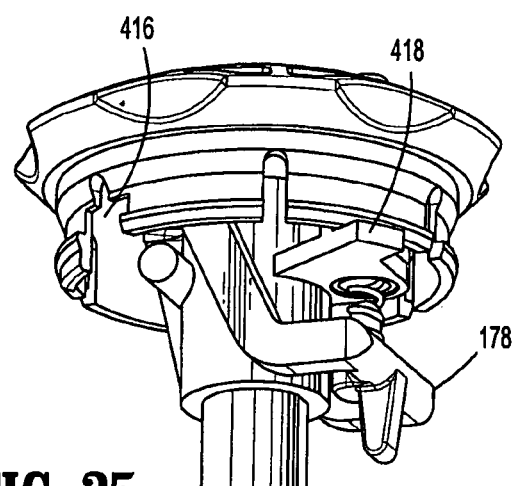
FIGS. 35-36 are views illustrating rotation of the obturator housing cover between respective lock and release positions relative to the indicator collar.
Figure 36:
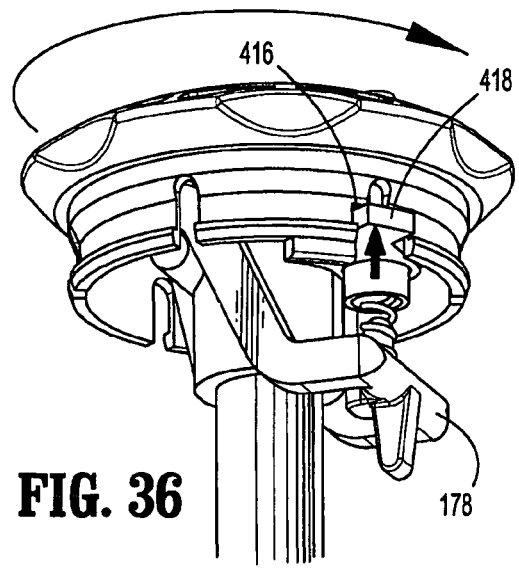
Figures 39, 40:
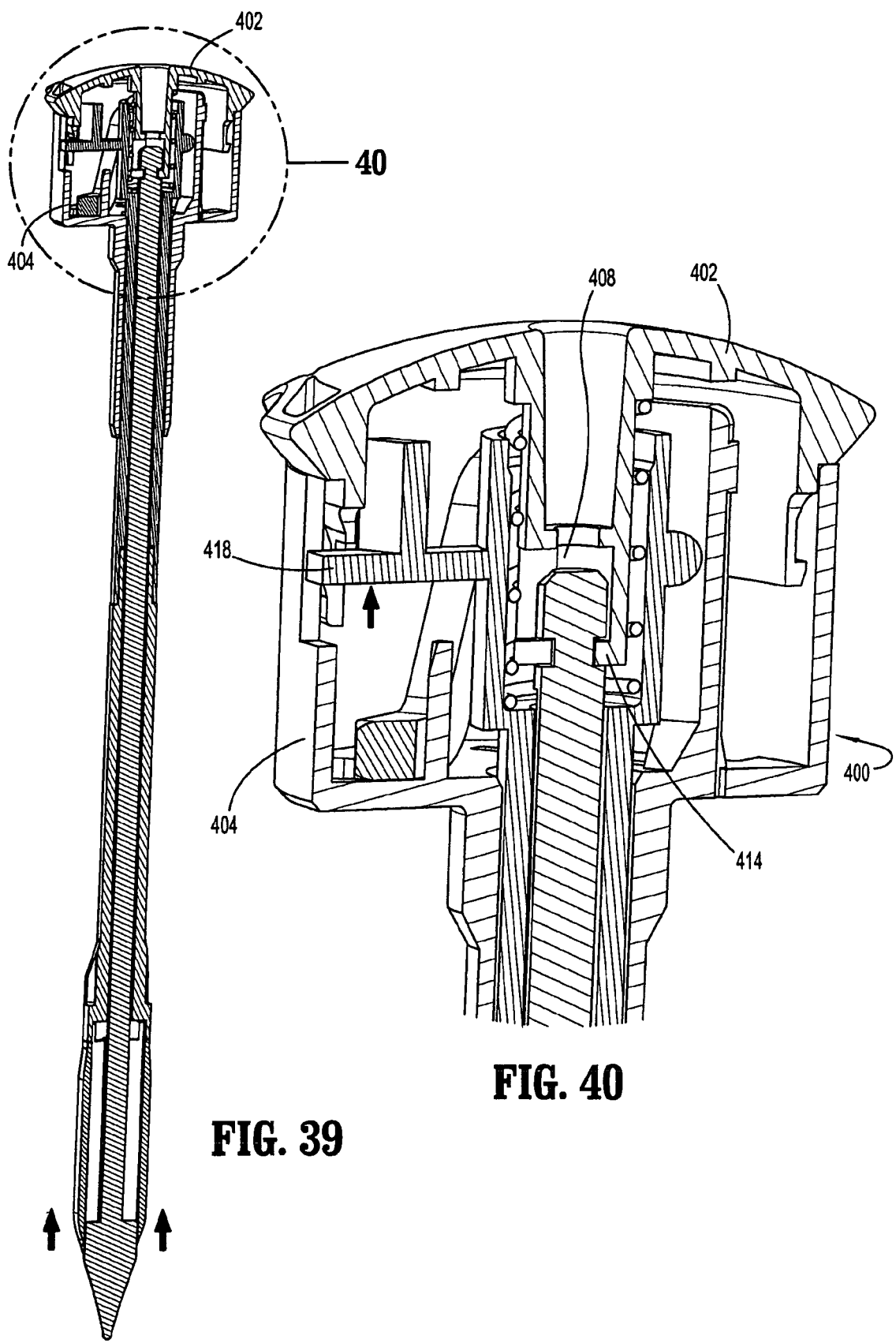
FIG. 39 is a side cross-sectional view illustrating the outer member retracted corresponding to an armed condition of the obturator member.
FIG. 40 is a view of the area of detail identified in FIG. 39.

Referring now to FIGS. 34-36, housing cover 402 further defines release groove 416 in its lower peripheral wall. In a locked position of housing cover 402 depicted in FIG. 35, release groove 416 is misaligned or displaced from indicator flag 418 of indicator collar 420 whereby the indicator flag 418 is engageable with the lower surface of the housing cover 402. Indicator flag 418 is initially disposed within slot 404a of housing base 404. Accordingly, indicator collar 420 is preventing from retracting thus preventing retraction of outer member 106. Upon rotation of housing cover 402 to the second release position depicted in FIG. 36, release groove 416 is aligned with indicator flag 418 of indicator collar 420 thereby permitting the indicator collar 420 to retract. Consequently, outer member 106 is permitted to retract to expose the penetrating member as shown in FIGS. 39-40.

Figure 38:
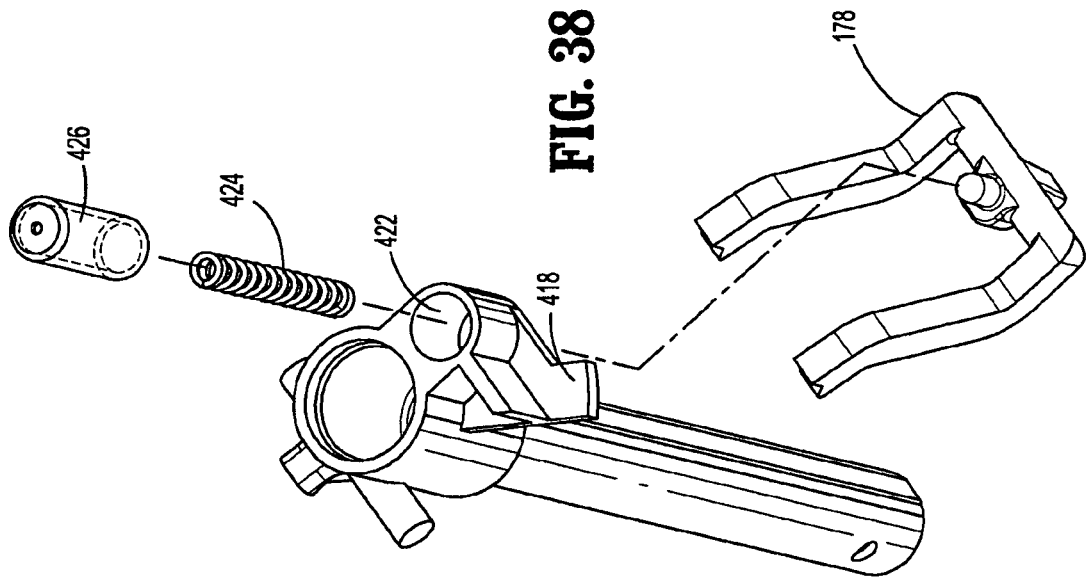
FIG. 38 is a perspective view of the latch collar, indicator collar and spring of the obturator assembly of FIG. 31.
Figure 37:
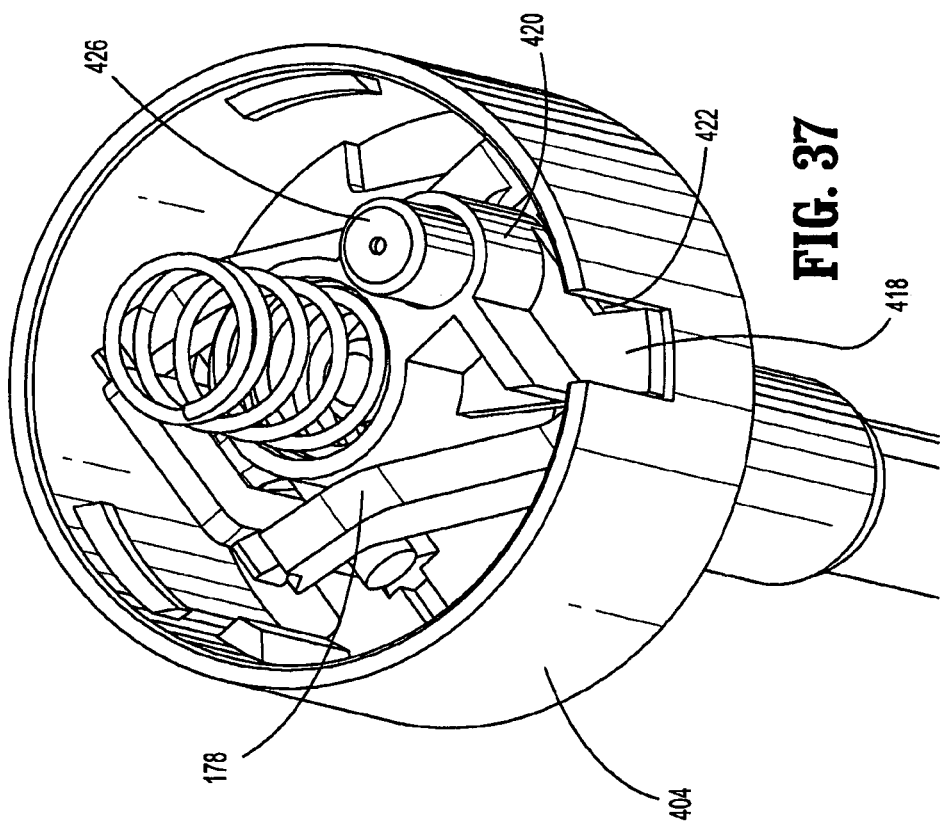
FIG. 37 is a perspective view of the obturator housing base.

FIG. 38 illustrates indicator collar 420 in greater detail. As shown, indicator collar 420 includes aperture 422 which accommodates slider return spring 424. Return spring 424 has a cover 426 over its proximal end. Cover 426 provides some rigidity to return spring 424 to permit obturator housing cover 402 to slide relative to return spring 424 during movement between the locked and unlocked position without affecting the integrity of the return spring 424. For example, cover 426 provides a non obtrusive surface upon which the housing cover may slide.

In other respects, obturator housing functions in a similar manner to the obturator assembly of FIGS. 1-23.

The materials utilized in the components of the presently disclosed trocar assembly generally include materials such as, for example, ABS, polycarbonate, stainless steel, titanium and any other suitable biocompatible metals and/or polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A surgical system for penetrating tissue, which comprises an obturator including:
   an obturator housing;
   an obturator member extending from the obturator housing, the obturator member including an obturator rod and a leading penetrating member and defining a longitudinal axis along which the obturator rod extends from trailing to leading ends thereof, the leading penetrating member adapted to penetrate tissue, the penetrating member defining, from leading to trailing, a cylindrical element having a generally arcuate leading surface and a generally planar dissecting element extending from the cylindrical element, the planar dissecting element being longitudinally spaced relative to the leading end of the cylindrical element, to permit the cylindrical element to perform initial dissection of tissue during advancement of the penetrating member in tissue, the obturator rod and the leading penetrating member being monolithically formed; and
   a distal nose having a central aperture and at least one slot longitudinally spaced from the central aperture, the central aperture of the distal nose configured to receive at least a portion of the cylindrical element therethrough and the at least one slot of the distal nose configured to receive at least a portion of the planar dissecting element therethrough, the distal nose being adapted for longitudinal movement between a first fully extended position corresponding to a first operative condition of the penetrating member and a second retracted position corresponding to a second operative condition of the penetrating member, the distal nose being normally biased toward the first fully extended position.

2. The surgical system according to claim 1 wherein the obturator rod defines a generally "t"-shaped cross-section along a substantial length thereof.

3. The surgical system according to claim 1 wherein the generally planar dissecting element defines side surfaces obliquely arranged with respect to the longitudinal axis.

4. The surgical system according to claim 3 wherein the side surfaces are arcuate.

5. The surgical system according to claim 3 wherein the side surfaces define cutting edges.

6. The surgical system according to claim 3 including an outer member mounted about the obturator member, the distal nose coupled to a distal end of the outer member, the outer member being adapted for longitudinal movement with the distal nose.

7. The surgical system according to claim 6 wherein the outer member is normally biased toward a position corresponding to the first position of the distal nose.

8. The surgical system according to claim 7 wherein the penetrating member is dimensioned whereby the cylindrical element and the side surfaces each are at least partially exposed from the distal nose when the distal nose is in the second position.

9. The surgical system according to claim 7 wherein the penetrating member is dimensioned whereby the cylindrical element is at least partially exposed from the distal nose when the distal nose is in the first position, to assist in initial dissection of tissue.

10. The surgical system according to claim 9 wherein the obturator member defines proximal and distal ends, the proximal and distal ends corresponding to the trailing and leading ends, respectively.

11. The surgical system according to claim 7 including a cannula defining a longitudinal axis and having a longitudinal opening therethrough for at least partial reception of the obturator.

12. The surgical system according to claim 11 including a latch member associated with the obturator housing, the latch member being moveable from an initial position securing the outer member and the distal nose in the first position to a release position permitting the outer member and the distal nose to move to the second position.

13. The surgical system according to claim 12 including a release member mounted to the obturator housing and operatively coupled with the latch member, the release member adapted to move the latch member to the release position during positioning of the obturator within the longitudinal opening of the cannula.

14. The surgical system according to claim 12 wherein the obturator housing includes a housing base and a housing cover, the housing cover adapted for rotation about the longitudinal axis between a lock position preventing movement of the outer member and the distal nose and a release position permitting the outer member and the distal nose to move to the second position.

15. The surgical system according to claim 6 wherein the generally arcuate leading surface of the cylindrical element is dimensioned to extend from the central aperture of the distal nose when the distal nose is in the first fully extended position and in the second retracted position.

16. The surgical system according to claim 1 wherein the cylindrical element has a leading segment formed therewith defining a constant radius of curvature, the leading segment defining the arcuate leading surface.

17. The surgical system according to claim 1 wherein the planar dissecting element is generally atraumatic to tissue.

18. The surgical system according to claim 1, wherein the at least one slot is separate from the central aperture.

19. The surgical system according to claim 1 wherein the obturator member is longitudinally fixed relative to the obturator housing.

20. A surgical system for penetrating tissue to access an underlying operative site, which comprises:

an obturator including:
- an obturator housing;
- an obturator member extending from the obturator housing, the obturator member defining a longitudinal axis along which the obturator member extends and having proximal and distal ends, the obturator member defining a "t"-shaped cross-section along a substantial length thereof, the obturator member being longitudinally fixed relative to the obturator housing; and
- a penetrating member mounted to the distal end of the obturator member, the penetrating member dimensioned to penetrate tissue, the penetrating member defining, from distal to proximal:
  - a cylindrical element having a generally arcuate end surface and being dimensioned to extend along the longitudinal axis, the cylindrical element dimensioned to perform initial dissection of tissue; and
  - a generally planar dissecting element spaced with respect to the longitudinal axis a predetermined distance from the end surface of the cylindrical element, the dissecting element including side surfaces obliquely arranged with respect to the longitudinal axis and depending outwardly from the cylindrical element, the side surfaces dimensioned to penetrate tissue subsequent to the initial dissection performed by the cylindrical element as the penetrating member is advanced within the tissue; and an outer member mounted about the obturator member and including a distal nose having a central aperture and at least one slot longitudinally spaced from the central aperture, the outer member being adapted for longitudinal movement relative to the obturator housing between a first distalmost position corresponding to a first operative condition of the penetrating member in which the cylindrical element of the penetrating member is at least partially exposed through the central aperture of the outer member to permit the initial dissection of tissue, and a second proximal position corresponding to a second operative condition of the penetrating member in which the side surfaces of the penetrating member are at least partially exposed through the at least one slot of the outer member.

21. The surgical system according to claim 20 wherein the outer member is normally biased toward the first distalmost position.

22. The surgical system according to claim 20 wherein the cylindrical element has a leading segment formed therewith defining a constant radius of curvature, the leading segment defining the arcuate end surface.

23. The surgical system according to claim 20 wherein the planar dissecting element is generally atraumatic to tissue.

24. The surgical system according to claim 20, wherein the at least one slot is separate from the central aperture.

* * * * *